United States Patent [19]

Weick

[11] Patent Number: 5,016,425

[45] Date of Patent: May 21, 1991

[54] DISPENSER FOR THE VAPORIZATION OF ACTIVE SUBSTANCES TO BE INHALED

[76] Inventor: Heinz H. Weick, 94, rue de la Servette, 1202 Geneva, Switzerland

[21] Appl. No.: 525,064

[22] Filed: May 18, 1990

Related U.S. Application Data

[62] Division of Ser. No. 327,128, Mar. 22, 1989, Pat. No. 4,955,945.

[30] Foreign Application Priority Data

Jul. 13, 1988 [CH] Switzerland .................. 02661/88
Sep. 19, 1988 [CH] Switzerland .................. 03483/88
Dec. 21, 1988 [CH] Switzerland .................. 04713/88

[51] Int. Cl.$^5$ ............................................. B65B 47/10
[52] U.S. Cl. ..................................... 53/453; 53/559; 53/471; 53/282
[58] Field of Search ............... 53/453, 454, 471, 559, 53/560, 282

[56] References Cited

U.S. PATENT DOCUMENTS

| | | | |
|---|---|---|---|
| 2,700,939 | 2/1955 | Liston | 53/559 X |
| 2,775,080 | 12/1956 | Stirn | 53/454 X |
| 3,924,636 | 12/1975 | Addison . | |
| 3,950,919 | 4/1976 | Perdue | 53/453 X |
| 4,223,512 | 9/1980 | Buchner | 53/453 X |
| 4,467,799 | 8/1984 | Steinberg . | |
| 4,627,432 | 12/1986 | Newell et al. . | |
| 4,711,237 | 12/1987 | Kaiser . | |
| 4,811,731 | 3/1989 | Newell et al. . | |
| 4,856,509 | 8/1989 | Lemelson . | |

FOREIGN PATENT DOCUMENTS 2184016 6/1987 United Kingdom .

Primary Examiner—John Sipos
Attorney, Agent, or Firm—Fleit, Jacobson, Cohn, Price, Holman & Stern

[57] ABSTRACT

A dispenser for an active substance which is positioned in the region of the nostrils for inhalation and is used for the evaporation of active substances of a medicinal, paramedicinal, and flavor-therapeutic types. The dispenser includes a flat dish that is made of absorbent, air-penetrable material and is surrounded by a circular edge. The dish is covered by a lid that is pasted on the edge. Loosely poured micro-capsules containing an active substance are contained in a closed chamber formed between the lid and the dispenser. A central area of the outside of the lid is covered with a tampon-like adhesive layer which, in turn, is covered by a peelable siliconized protective foil. A process and a production line for the manufacturing of the dispenser of active substances are described.

18 Claims, 3 Drawing Sheets

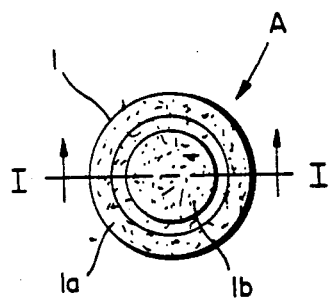
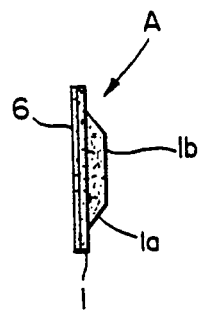
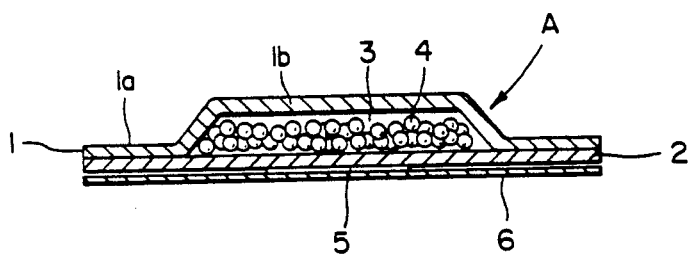
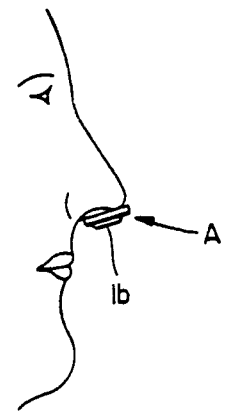
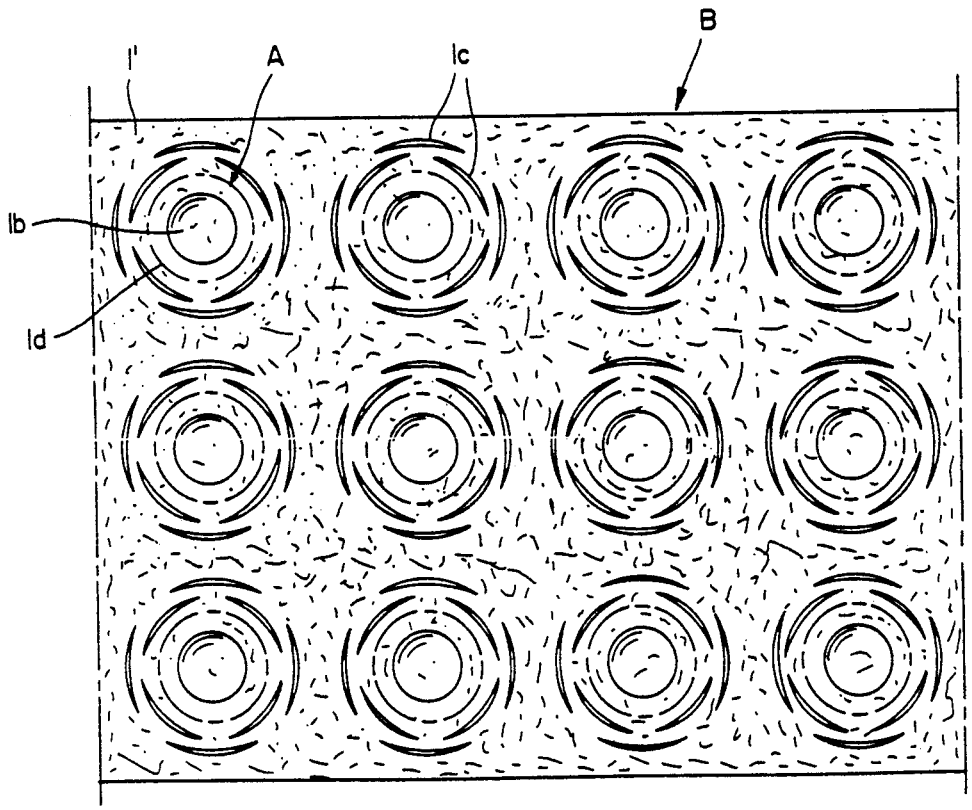

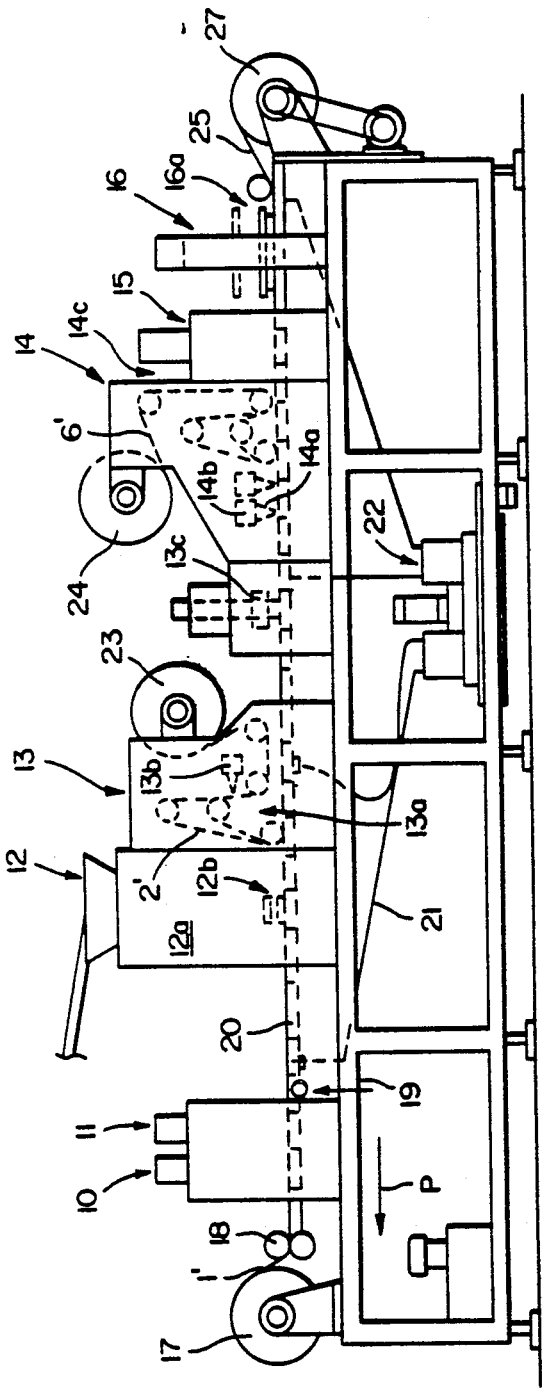
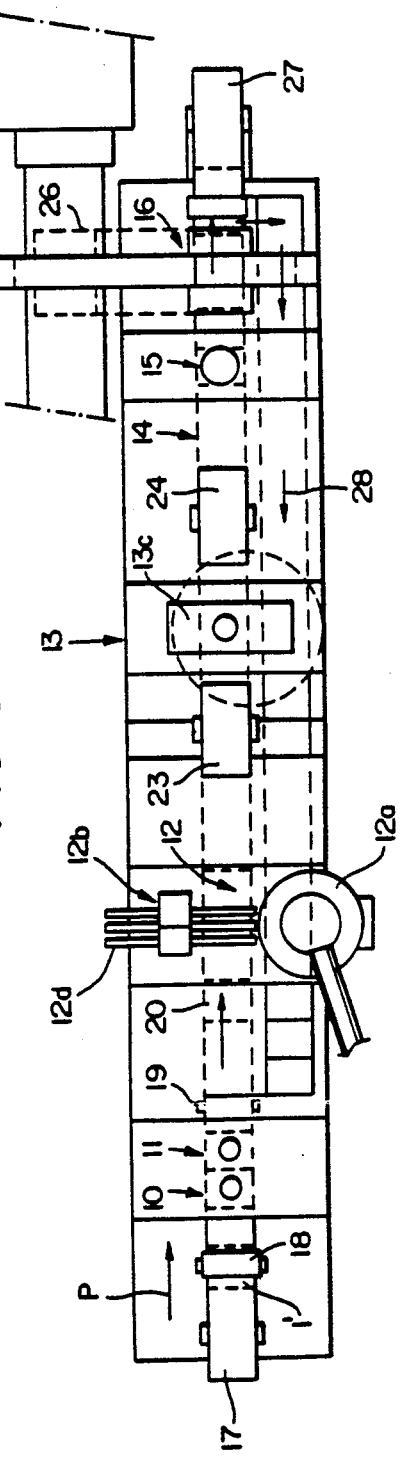
FIG. 5
FIG. 6

DISPENSER FOR THE VAPORIZATION OF ACTIVE SUBSTANCES TO BE INHALED

This is a divisional application of application U.S. Pat. No. 07/327,128, filed Mar. 22, 1989, now U.S. Pat. No. 4,955,995.

Field of the Invention

The invention is concerned with a dispenser to be placed within the area of the nostrils. Active substances in the dispenser, of a medical, paramedical, and aromatic-therapeutic nature, are vaporized and then inhaled. The invention includes a hollow body containing the active substance and having at least one absorbent evaporation wall that releases the active substance into the air which is inhaled during respiration.

BACKGROUND OF THE INVENTION

There is a great need for simple means for self-medication involving the inhalation of active substances, either for the effective treatment of an inflamed respiratory tract or for the alleviation of the discomforts of asthma. In addition, aromatic therapy treatment for stress, sleeping disorders, etc. is becoming more and more important.

The dispensers of active substances of the aforementioned type have not been successful in the marketplace up to this time, even though generations of various designs have become known. The reasons for their failures vary widely. Their spatial forms are sufficiently large and therefore make proportionally large demands during their production, which is reflected in a prohibitively high price.

As to positioning, two variations are commonly used: in the first variation, the dispenser is placed under the nose and fastened by means of a band around the head, while in the second variation, the dispenser is inserted, at least partially, into the nostrils and is kept there in a self-clipping manner. Accordingly, other aesthetic requirements are not met due to the large tri-dimensional spatial form and fastening band, or else physiological conditions such as irritating contact with the mucous membrane of the nose, difficulty of breathing, hindrance in case of head cold are not encountered. In addition, the storage of the active substance in the dispensers is poor. When the dispenser is filled by the manufacturer with an active substance, an individual gas-tight package prevents any evaporation during transport and storage. The intensity of evaporation cannot be dosed, even though not every user desires equally strong application of the active substance. On the other hand, a dispenser which the user activates by dripping the substance, is not practical. In particular, it can hardly be expected that children, sick and old people can perform such a manipulation. In addition, if the outside of the dispenser is wetted during such an operation, unpleasant skin irritations will result.

SUMMARY OF THE INVENTION

This invention is based on the problem of eliminating all shortcomings of the designs proposed up to this time and to develop a dispenser for active substances that is distinguished, in every respect, by a non-comprising design that may be manufactured in large numbers and, therefore, at a very low cost. The invention lies in the fact that the hollow body which has been designed as a small hollow plate includes a flat dish which is made of absorbent, air-penetrable material. The dish has a circular edge covered by a pasted-on lid and, with it, a chamber is encircled that is filled with micro-capsules containing active substances. The lid is provided with an adhesive layer that adheres to the skin and is protected by a peelable foil.

The active agent of the dispenser designed in this way is enclosed in the micro-capsules, in a way that is practically gas-tight, so that, if one wishes to have a gas-tight outer package, a double gas barrier is achieved. The dispenser is activated immediately before its use, by the user compressing the small hollow plate, e.g. between thumb and forefinger. This compression of the chamber housing the micro-capsules causes the micro-capsules to burst. The active substances flowing from the dispenser are absorbed by the deformed absorbent layer. Since the absorbent layer absorbs the active substance and evaporates the active substance over its entire surface, the effective evaporation surface is maximized. Inasmuch as, by choice, a larger or smaller part of the micro-capsules is crushed, the vaporization is more or less intensive and variable, and it is possible to activate the dispenser several times at any chosen time.

The production of the micro-capsules takes place, at low cost in large quantities, in known devices. After the protective foil has been peeled off, the dispenser will, in the simplest way, adhere by means of self-sealing be positioned below the nasal septum, the nasal cartilage, or on the upper lip. The dispenser will be worn there, due to its thin spatial form and small surface areas, discreetly and retain its position while the wearer is asleep. The air of respiration that moves along the evaporation surface is not impeded in any disturbing way. There is no contact with the mucous membrane of the nose. Accordingly, any physiological side effect is prevented.

As is evident from the following, the air penetrability of the dish is an essential design characteristic of the product, inasmuch as its manufacture is concerned. Basically, it is known how to design dispensers of active substances to be placed in the region of nose and mouth in such a way that they have the form of little flat plates. But, they have been developed in a different way, are worn in medical napkins and are not subject to the pass-through of the air of respiration.

Their disadvantages are in the difficulty of their use, the conspicuous appearance when in use, and the considerable hindrance of the air of respiration. Although one of the dispensers of active substances contains micro-capsulated active substance (Japanese Trademark #54-3595), the products are of a different kind with the aforementioned specific disadvantages. In addition, in the dispenser in accordance with the aforementioned Trademark, the micro-capsules are stored first in a filling of absorbent textile material which, in turn, is enveloped by two perforated dishes fastened to one another. Moreover, the textile filling holds back, unnecessarily, the less readily evaporating components of the active substance that obviates the most desirable steady vaporization.

In addition, it should be mentioned that dispensers of active substances that are used for deodorizing, for applying perfume, as well as for the vaporization of insecticides, that have a flat plate-like shape, and that are to be pasted on clothing or, e.g., in the armpit, have nothing to do with "self-medication" but with general cosmetics or with the repelling of insects, and are concerned with another class of products. Moreover, the design as well as the type and positioning of the active agent within a small hollow plate, and thereby also their manufacturing method, differ from the product in accordance with the invention.

In accordance with the invention, the method for the automatic production of the dispenser of active substances includes a layer of absorbent air-penetrable material receiving, first, by means of a pressing device, at least one dish-like deformation on which subsequently micro-capsules are placed by means of a filling device, and on which then a second layer is pasted, that constitutes the lid, by means of a first lining device, while subsequently a device for the application of adhesives provides the outside of the second layer with an adhesive layer that is coated, by means of a second lining device, with a peelable protective foil. The dish-like deformation is subjected — at least, before the placing of the micro-capsules, until the second layer is pasted over — through an "inverse bearing bed" of a bearer plate, to an indraft that flows through the air-penetrable material in the region of the deformation. This method solves, among other things, the difficult problem of manipulating the tiny micro-capsules which are light and, therefore, have a tendency to scatter, in the simplest and safest way. By subjecting the beds of the bearer plates to the indraft flowing through the absorbent layer within the region of the deformation, the micro-capsules which are poured loosely from above, are sucked into the deformation without any tendency to scatter, and are held within the deformation so securely, that he bearer plate may be moved subsequently, with great acceleration, to the next station of the production line. In addition, the aforementioned exposure to an indraft brings about a firm lock that will respond to traction —of the position of the deformed layer in the bearer plate, so that the flow of material will take place automatically when the bearer plate is moved.

A method of producing, in accordance with the invention, is characterized by a die stamp for the dish-like deformation of a layer of absorbent, air-penetrable material. The die stamp is followed by a filling device for placing the micro-capsules on the dish-like deformation. The filling device is followed by a first lining device for pasting a covering layer over the filled deformation which acts as a lid. The lining device is followed by a device for the application of an adhesive layer on the outside of the covering layer. A second lining device is designed to cover the adhesive layer with a peelable, silicon-like protective foil. A device automatically removes the finished dispenser.

Bearer plates may be moved in the direction of the flow of the material from the die stamp to the device for the removal of the material. The bearing plates receive the dish-like deformation in "inverse bearing beds" that are air-penetrable, and the underside of which are connected with a device for the application of an indraft.

Additional characteristics of the dispenser of active substances, the method of its production, the production line for the execution of the method, and further advantages resulting therefrom are evident from the description of the Figures.

BRIEF DESCRIPTION OF THE DRAWINGS

The drawings show examples of the embodiments of the invention.

FIG. 1 is a plan view of a dispenser of active substances in accordance with the invention;

FIG. 2 is a lateral view according to FIG. 1;

FIG. 3 is a cross sectional view taken along line I—I according to FIG. 1;

FIG. 4 is a facial profile of a person wearing a dispenser of active substances in accordance with FIGS. 1-3;

FIG. 5. is a lateral view of a schematically drawn production line for the automatic production of the dispenser of active substances in accordance with the invention;

FIG. 6 is a plan view according to FIG. 5;

FIG. 10 is a plan view of an assembly block including several dispensers of active substances.

DETAILED DESCRIPTION OF THE PREFERRED EMBODIMENTS

Figure 7A:
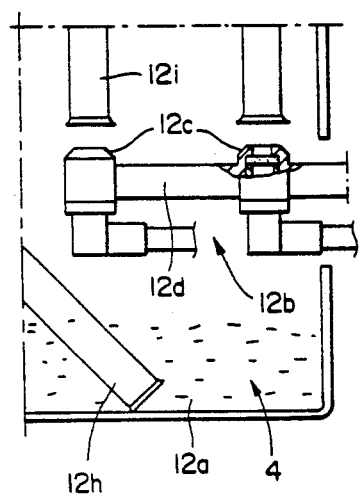
FIGS. 7a -7c illustrate placing micro-capsules on the deformed layer.
Figure 7B:
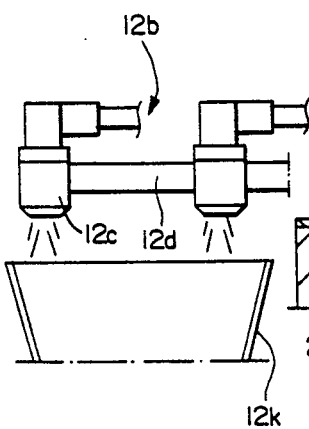

The dispenser of active substances in accordance with FIGS. 1 to 4 comprises, first, a flat dish 1 having a deformation 1b that is surrounded by a circular edge 1a and is made of absorbent, air-penetrable material such as unsized, slightly pressed paper, blotter or similar materials and closed by means of a small lid 2, e.g., made of the same material, and pasted on the edge 1a. In the closed chamber 3 which is formed between dish 1 and lid 2, there are, loosely poured, micro-capsules 4 filled with medicinally active substances; the diameter of the capsules is, e.g., 500 to 800$\mu$. The outside of the lid 2 is coated, in its central area, with a tampon-like adhesive layer 5 which, in turn, is covered by a peelable, siliconized protective foil 6.

In order to activate the dispenser of the active substance, the active substance is freed by manual pressure on the dish 1, i.e., by crushing the micro-capsules 4. The active substance is immediately led outwardly by the absorbent material of the dish 1, for its vaporization.

After the user has removed the protective foil 6, the user pastes the dispenser, in accordance with FIG. 4, below the nasal septum, the nasal cartilage, or on the upper lip. When the dispenser is positioned in that way, respiration air flows along the outside of dish 1 and absorbs active substance which, thereby, arrives in the body by the shortest possible route. Active substances of a medical and paramedical nature, such as eucalyptus oil, are used in treatment of inflammatory diseases of the respiratory tract, as well as for aromatic therapy, which is being used more and more.

The advantages of a dispenser of active substances are that until its use, the active substance is enclosed gas-tight in the micro-capsules 4, so that no gas-tight outer packaging is required. The activation of the active substance takes place by means of a simple manual pressure on the dish 1, whereby the micro-capsules are crushed. The entire surface of the dish 1 aids in evaporating the contents of the micro-capsules by increasing the exposed surface area.

The vaporization medication may be dosed by crushing, at desired time intervals, part of the micro-capsules 4 by applying light pressure to the dish 1 each time.

The positioning by self-adhesion is the simplest possible solution and can be repeated several times when, in each case, only part of the micro-capsules of the same dispenser are activated. Due to the practically flat design, the dispenser may be worn discreetly and does not interfere with sleep. Practically, there is neither any impedance of the air for respiration nor any contact with the mucous membrane, and physiological side effects have therefore been eliminated.

The air-permeability of the dish 1 and its punched-out portion for receipt of micro-capsules, as well as adhesive layer 5 being smaller than the diameter of the dispenser, make mass production possible at extraordinarily low cost.

The protective foil 5 may be sized for easy removal from the circumference of the dispenser.

The production line, as shown schematically in FIGS. 5 and 6, for the manufacture of the dispenser takes place by means of a fixed-cycle control, i.e., the movement of the material takes place step-by-step. The direction of the flow of the material is indicated by the arrow P. FIGS. 7a to 7c, 8 and 9 show, in a more complete presentation, particularly important design details.

The production line comprises the following essential devices, as arranged behind one another, in the direction P of the flow of material: Punching device 10 for the production of cross-section 1c in the layer 1' of absorbent, air-permeable material; die stamp 11 for the production of the dish-like deformations 1b in the aforementioned layer; filling device 12 for placing the micro-capsules 4 on the dish-like deformations 1b; first lining device 13 for pasting a covering layer 2' over the layer 1' containing the micro-capsules 4; second lining device 14 for the tampon-like application of an adhesive layer 5 on the covering layer 2' and covering of the adhesive layer 5 by means of a peelable protective foil 6'; punching device 15 for punching-out the finished dispenser A, as well as a device for its automatic removal. The layer 1' of absorbent, air-permeable material (e.g., unsized or blotting paper) is diverted by means of the guide roller 18 from the pivoting roll of material 17 to the punching device 10.

The manufacture takes place by blocks, i.e. each operation is concerned, at the same time, with several dispensers A that are to be produced, and are interconnected in lengthwise and transverse rows within assembly block B, and finally are punched out of block B. The number and mutual distance of the dispensers A of an assembly block are determined by the volume of the packaging unit. When the production line is of suitable size, it is of course possible, in order to reduce the cost of production even more while increasing capacity at the same time, to produce several assembly blocks, i.e., a group of assembly blocks per work cycle. The useful deformation of layer 1' of the size of an assembly block and consisting of absorbent, airpermeable paper that is, when dry, hardly drawable, is per se possible only during the manufacture of the paper and is, therefore, rather complicated. That handicap is circumvented by the punching device 10. In accordance with FIG. 10, it punches out the overlapping, coaxial free sections 1c into a surface area dimensioned for an assembly block B and/or for a group of assembly blocks of the pertinent layer 1' at a distance around each dish-like deformation 1b to be produced, so that the subsequently produced deformations 1b are connected in a straplike manner together.

During the deformation by the die stamp 11, the free sections 1c pull apart to the extent required, so that a capacity for being drawn is not necessary.

Within the region of the die stamp 11, there is at least one lifting roll 19 that runs athwart the flow of movement, grips the layer 1' from below, and may be moved vertically. By means of the roll 19, the aforementioned layer may be lifted, for its further movement, out of the matrix of the pressing die (not shown). The lifting roll 19 is equipped with annular tee-slots (not shown) through which the deformations 1b can slide unimpeded.

After the moving step and the redescending of the lifting roll 19, the deformed layer 1' is received by a bearer plate 20. Several such bearer plates 20 take over the moving of the material and are moved, step-by-step, from the die stamp 11 to the removing device 16, in order to be moved from there, on a cyclical course, on the parallel route 28, to the starting point. The bearer plates 20 have supporting beds 20a for holding the deformations 1b. The supporting beds 20a may, if necessary, be subjected to indraft or compressed air, from below through an air-permeable insert 20b made of sintered metal, through a bore 20c, by means of ducts 21 and by way of a rotary platen 22. When subjected to an indraft, the deformed layer 1' is secured in its position on the bearer plate 20, in such a way that the bearer plate 20 automatically pulls the paper to secure the paper in position.

The filling device 12 comprises an apportioning container 12a mounted laterally in relation to the production line and an apportioning member 12b that has a siphon-like effect and may be moved to and fro between the apportioning container 12a and the bearer plate 20 which takes over the filling material in each case.

Figure 7C:
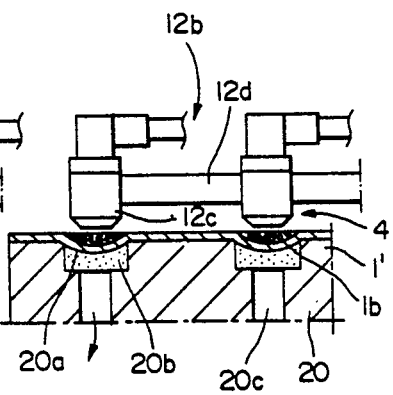
Figure 8:
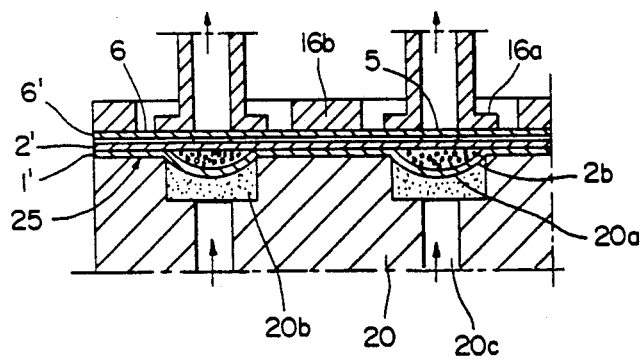
FIG. 8 is an enlarged section of a detail of the device for placing the micro-capsules according to FIGS. 7a-7c.

The bearer plates 20 have bearer beds 20a for holding the deformations 1b. The apportioning member 12b is equipped with apportioning heads 12 whose number and arrangement in relation to one another corresponds to the deformations 1b of an assembly block B, or to a group of assembly blocks B. The dosing heads 12c which, in each case, are mounted athwart the direction of the production line are mounted in rows on rotating shafts 12d. Each apportioning head 12c comprises a bottom that is open on one side and, e.g., a bottom consisting of a small inserted sintered-metal plate, and the bore 12f, if need be, by which an indraft or compressed air may be applied to the apportioning chamber 12g. The apportioning heads 12c are located, for the apportioned intake of the micro-capsules 4, in the apportioning container 12a (FIG. 7a) with apportioning-chamber openings pointed in an upward direction. Micro-capsules 4 are poured by a pneumatic transporting device 12h, 12i from above into the apportioning chambers 12g and are held in them by the simultaneous application of an indraft. Poured material that might overflow falls back into the apportioning container 12a below. Then, the apportioning member is moved over the bearer plate 20 that is subjected to an indraft and is to be filled, while at the same time the shafts 12d rotate by 180° (FIG. 7c). Inasmuch as the subjection of the apportioning heads 12c is interrupted, the micro-capsules 4 do not only drop into the deformations, but rather are sucked into them and their position is secured by the air-permeability of the paper of the deformations, without any scattering effect. Since some powdery substance is added to the micro-capsules 4, so as to prevent any mutual adhesion, the little plate of sintered metal 12c could become clogged, due to the indraft. In order to counteract that tendency, the apportioning heads 12c are dusted off by a short blow of compressed air on their way back to the apportioning container 12a above a funnel 12k.

By those means, the per se extremely difficult manipulation of the micro-capsules that tolerate only minimal mechanical stress, and that are scattered by the smallest breath of air, due to their extremely small size and small mass, are solved excellently. Their only mechanical stress is mutual friction and insignificant wall friction during pneumatic transport and in the apportioning chambers 12g. The bearer plates 20 can be moved to the next station at high speed; no micro-capsule will escape from the deformations 1b.

Within the lining device 13, the covering layer 2'—which, e.g., also is made of paper, is diverted from the pivoted roll of material 23 into the plane of the bearer plate, by means of the guide roller 13a. The underside of layer 2' is coated, by the device for the application of adhesive 13b, with hot, rapidly hardening adhesive. The mutual adhesive connection between the deformed layer 1' and the covering layer is established through the adhesive by means of heating reactivating dies 13c.

The second lining station 14 comprises a device for applying the adhesive 14b that is equipped with nozzle-like members 14a. By means of the nozzles, the covering layer 2' is provided, centrally above each deformation 1b, with a tampon-like adhesive point or dash 5. The siliconized protective foil 6' is applied subsequently from the pivoting roll of material 24, by way of the guide rollers 14c, to the covering layer 2' that has been equipped with adhesive tampons.

Now, the punching-out of all dispensers of active. substance A of the finished assembly block B or of the group of assembly blocks takes place by means of the punching device 15. Inasmuch as the adhesion between the deformed layer 1' and the covering layer 2' has been established by means of an immediately hardening — so-called "hot melt"— material, and inasmuch as the dispensers A which are to be punched out, have been provided centrally only with an adhesive layer 5, in a tampon-like way, the punching means do not come in any contact with adhesive material. In that way, the need for cumbersome continual cleaning is obviated and corresponding troubles are eliminated. Moreover, when the adhesive layer 5 is designed in this way, the protective foil 6 may be sized for removal over its entire circumference.

Figure 9:
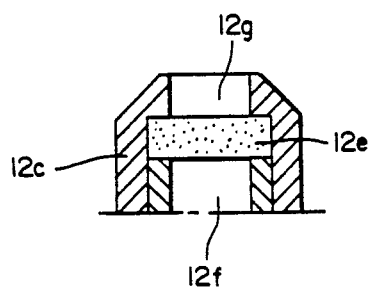
FIG. 9 illustrates the removal of the finished, punched-out dispenser of active substances shown in transverse section.

The removal device 16 which is designed as a manipulating means is equipped with small movable plates 16a which may be subjected to an indraft (FIG. 9). They are of the same number and mutual arrangement as the dispensers A that are present in an assembly block B or in a group of assembly blocks. While the small removal plates 16 suck in the dispensers A, and while the hold-down device 16b holds back the waste paper 25 of the assembly block A or of the group of assembly blocks, the bearer beds 20a of the corresponding bearer plate are subjected to indraft at the same time, so that the dispensers A are pressed additionally against the small removal plates 16a. In that way, the possibility of the protective foil 6 separating from the adhesive tampon 5 during this operation is obviated. The manipulating means 16 transfer the dispensers immediately into a package 26 which is supplied by an automatic packaging device. The waste paper which adheres in the form of a tape, is wound onto a roller 27.

An additional advantage of the production line may be achieved by a particular development of the filling station 12. In this design, the apportioning container 12a is equipped with several, e.g., three compartments for filling the apportioning chambers 12g with micro-capsules 4. In that way, it is possible, e.g., to position at the same time, micro-capsules containing various active substances and/or flavors. Each row of dispensers in the sales package 26 contains, in that way, a different active substance and/or an active substance with different flavor. The rows are identified approximately on the package. Consequently, the customer is able, e.g., in the case of self-medication, for tranquilization or against insomnia, to vary the active substance and/or the flavor.

I claim:

1. A method for the manufacture of a dispenser of active substances, said method comprising:
   receiving a first layer of absorbent air penetrable material,
   deforming the layer to form at least one dish-like deformation,
   placing micro-capsules in the deformation,
   pasting a second layer on the first layer to form a lid,
   providing an adhesive layer on the second layer,
   placing on adhesive layer a peelable protective foil that covers the entire second layer and which upon peeling the adhesive layer in an adhesive state,
   punching the peripheral area of said dispenser to separate the dispenser from said layers,
   subjecting the dish-like deformation at least, before the placing of micro-capsules on it, until the second layer is pasted over it, to an indraft that flows through the first layer within the area of the deformation,
   wherein the second layer located above the deformation is provided with the adhesive layer the surface area of which is smaller than the outline of the dispensers of active material, in such a way that the punched peripheral sections forming the dispensers of active substances will be located in zones that are free of adhesive layers.

2. A method in accordance with claim 1, wherein said subjecting to an indraft is changed to an exposure to compressed air at the time of the removal of the dispenser, so that the dispenser of the active substance is pressed out of a bearer plate.

3. A method in accordance with claim 1, wherein said placing of micro-capsules on the dish-like deformation takes place by a siphon-like apportioning member movable from an apportioning container to the dish-like deformation and back, and includes an apportioning chamber open on one side, and said apportioning chamber is subjected to an indraft on its way from the apportioning container to the dish-like deformation, while it receives a compressed-air impulse on the way back.

4. A method in accordance with claim 3, wherein the micro-capsules are poured into the apportioning chamber while the open side points in an upward direction and is subjected, at the same time, to an indraft, so that the apportioning chamber performs a turn of 180° during each forward and backward movement.

5. A method in accordance with claim 1, wherein several dispensers of active substance are made and are located at a distance from one another to form at least one assembly unit, arranged to be located side-by-side or behind one another, while the first layer of absorbent, air-penetrable material is provided, before the deforming step, with cross-sections around each dish-shaped deformation to be made, in such a way that all of the areas of said first layer which are surrounded by the cross-sections, and which are to be deformed into a dish-like shape, remain connected in a cross-piece linkage, and the dispensers of active substance are punched, after the peelable foil has been applied, from the assembly unit in circular sections.

6. A method in accordance with claim 1, wherein the pasting together of the deformed first layer with the second layer takes places by using an adhesive that will harden immediately after pasting.

7. A method in accordance with claim 1, wherein before the second layer is pasted together with the deformed first layer, the second layer is coated with an adhesive applied while hot and that the pasting together takes place by a reactivation of the adhesive layer achieved by supplying heat.

8. A production line for the manufacture of a dispenser of an active substance, said production line comprising:
a screw-press for forming dish-like deformations in a first layer of absorbent, air-penetrable material,
a filling device for placing micro-capsules in the dish-like deformations,
a first lining device linked to said filling device for pasting-over the filled deformation with a covering second layer,
a device for the application of an adhesive layer to the outside of the covering second layer,
a second lining device for covering the adhesive layer with a silicon-like, peelable protective foil that covers the entire second layer and which upon peeling leaves the adhesive layer in an adhesive state,
a punching device for the automatic removal of the finished dispenser of active material,
bearer plates movable in a direction of flow from said screw-press to said removal device for receiving the dishlike deformations in bearer beds that are air-penetrable, and
a pneumatic device for the imposition of an indraft to the undersides of said bearer beds,
wherein the device for the application of the adhesive layer in the outside of the covering second layer is constructed in such a way that the surface area of said adhesive layer is smaller than the outline of the dispenser of active material, so that punched peripheral sections forming the dispensers of active substances will be located in zones that are free of adhesive layers.

9. A production line in accordance with claim 8, wherein said bearer beds are formed of porous inserts such as perforated or sinter metal plates.

10. A production line in accordance with claim 8, wherein said pneumatic device for subjecting the bearer beds to an indraft contains means for switching to compressed air.

11. A production line in accordance with claim 8, wherein said filling device includes an apportioning member that is siphon-like and movable between the dish-like deformations and further including an apportioning container having a dosing chamber open on one side and said apportioning chamber being connected with a reversible indraft, compressed air system.

12. A production line in accordance with claim 11, wherein said siphon-like apportioning member is supported to be swung and/or rotated by 180°, and said apportioning member assuming during apportioning in said apportioning container, a position in which said apportioning chamber points in an upward direction, and said apportioning container including a device for the pneumatic protection of the apportioning chamber from loss of micro-capsules.

13. A production line in accordance with claim 11, wherein said siphon-like apportioning member has a porous insert such as perforated or sinter metal plates.

14. A production line in accordance with claim 8, wherein said first lining device for pasting over the filled deformations with the covering second layer contains compressing means such as a hot-die and/or ultrasound-sonotrode for reactivating a hardened adhesive layer that has been applied previously to said covering second layer.

15. A production line in accordance with claim 8, wherein several dispensers of active substance are formed from a continuous assembly block, the dispensers are positioned in said block in longitudinal rows and cross rows in relation to one another, and a punching device comprising one punch for each dispenser of active substance from the assembly block is positioned in front of said screw-press, while the punches are mounted in relation to one another, in such a way that they provide cross sections around each deformation to be formed in such a way that all surface areas are interconnected by crosspieces, and a die stamp is mounted in front of the removal device, for punching-out the finished dispensers of active substance from the assembly block.

16. A production line in accordance with claim 8, wherein said screw-press is combined with, at least, one lifting member for holding said first layer from below, said lifting member being movably supported between a position lower than the surface of a matrix plate of said screw-press and a position projecting above the surface of the matrix plate by, at least, the extent of the depth of the concavities of the matrix plate, so as to lift said first layer out of said matrix plate for further transport, after said first layer has been deformed.

17. A production line in accordance with claim 16, wherein said lifting member is in the form of a rod mounted athwart a direction of the flow of material along the production line, and is provided with recesses for the passage of the deformations during further transport of the deformed first layer.

18. A production line in accordance with claim 11, wherein said apportioning container includes at least two separate compartments for providing, at the same time, several apportioning chambers of said apportioning member with microcapsules filled with various active substances.

* * * * *